(12) United States Patent
Villarruel et al.

(10) Patent No.: US 8,651,138 B2
(45) Date of Patent: Feb. 18, 2014

(54) TUBULAR ARRAY FOR FLUIDIC FOCUSING WITH INTEGRATED OPTICAL ACCESS REGION

(75) Inventors: Carl A. Villarruel, Burke, VA (US); Janet W. Lou, Springfield, VA (US); Ross Schermer, Springfield, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 59 days.

(21) Appl. No.: 13/309,830

(22) Filed: Dec. 2, 2011

(65) Prior Publication Data

US 2012/0138152 A1 Jun. 7, 2012

Related U.S. Application Data

(60) Provisional application No. 61/418,966, filed on Dec. 2, 2010.

(51) Int. Cl.
| | |
|---|---|
| *E03B 1/00* | (2006.01) |
| *G01N 21/00* | (2006.01) |
| *F17D 1/00* | (2006.01) |
| *F17D 3/00* | (2006.01) |
| *G01N 33/00* | (2006.01) |
| *B01L 3/00* | (2006.01) |

(52) U.S. Cl.
USPC ............. 137/602; 137/2; 137/3; 422/68.1; 422/81; 422/82.05; 422/502; 422/504

(58) Field of Classification Search
USPC ......... 422/68.1, 81, 82.05, 502–504; 137/2, 3
See application file for complete search history.

(56) References Cited

U.S. PATENT DOCUMENTS

| | | | | |
|---|---|---|---|---|
| 6,083,763 | A * | 7/2000 | Balch | 506/9 |
| 2005/0123450 | A1* | 6/2005 | Gilbert et al. | 422/81 |
| 2008/0160603 | A1* | 7/2008 | Sundararajan et al. | 435/288.5 |
| 2008/0261295 | A1* | 10/2008 | Butler et al. | 435/286.5 |
| 2008/0311005 | A1* | 12/2008 | Kim et al. | 422/82.05 |
| 2009/0066936 | A1* | 3/2009 | Huang et al. | 356/73 |
| 2009/0201504 | A1 | 8/2009 | Ho et al. | |
| 2009/0208372 | A1* | 8/2009 | Mott et al. | 422/68.1 |
| 2010/0315639 | A1* | 12/2010 | Muraki | 356/342 |
| 2011/0294139 | A1* | 12/2011 | Takeda | 435/7.1 |

OTHER PUBLICATIONS

Written Opinion of the International Searching Authority, PCT/US2011/062999.
International Search Report, PCT/US2011/062999.

(Continued)

*Primary Examiner* — Bobby Ramdhanie
*Assistant Examiner* — Jennifer Wecker
(74) *Attorney, Agent, or Firm* — US Naval Research Laboratory; Roy Roberts

(57) ABSTRACT

An apparatus for creating sheathed flow includes an inlet section comprising an array of tubes including at least one sheath inlet port and a sample inlet port, a flow focusing section downstream from the inlet section, an optical access section downstream from the flow focusing region and comprising opposing flat surfaces, and an outlet section downstream from the optical access section, wherein the apparatus is operable to create a sheathed flow around a fluid introduced into the sample inlet port and to maintain the sheathed flow through the optical access section. Applications of the apparatus and method include bead/particle counting, flow cytometry, waveguiding, and fluid control.

18 Claims, 4 Drawing Sheets

(56) References Cited

OTHER PUBLICATIONS

Y. Zhao, B. S. Fujimoto, G. D. M. Jeffries, P. G. Schiro and D. T. Chui, "Optical gradient flow focusing", Optics Express, vol. 15, No. 10, pp. 6167-6175 (2007).

P. B. Howell, J. P. Golden, L. R. Hilliard, J. S. Erickson, D. R. Mott and F. S. Ligler, "Two simple and rugged designs for creating microfluidic sheath flow", Lab Chip, vol. 8, pp. 1097-1103 (2008).

G. Goddard, J.C. Martin, S. W. Graves and G. Kaduchak, "Ultrasonic particleconcentration for sheathless focusing of particles for analysis in a flow Microstructure", Cytometry Part A, vol. 69A, pp. 66-74 (2006).

R. Miyake, H. Ohki, I. Yamazaki and R. Yabe, "Development of Micro Sheath Flow Chanbers," Proc. of IEEE Micro Mechanical Systems Workshop, Nara, Japan, pp. 259-264 (1991).

\* cited by examiner

US 8,651,138 B2

TUBULAR ARRAY FOR FLUIDIC FOCUSING WITH INTEGRATED OPTICAL ACCESS REGION

CROSS-REFERENCE TO RELATED APPLICATIONS

This non-provisional application claims benefit of priority to Provisional Application Ser. No. 61/418,966 filed on Dec. 2, 2010, incorporated herein by reference.

BACKGROUND

Laminar flow, including sheath flow, is a technique useful in a variety of applications, including bead/particle counting, flow cytometry, waveguiding, and fluid control. Sheath flow involves surrounding a central flow stream (the core) with a surrounding stream (the sheath), wherein fluidic (e.g., hydrodynamic) forces compress the core flow stream into a narrow region. This permits the counting, detection, and/or sorting of a sample in the core, such as particles, beads, cells, and the like. In particle counting and flow cytometry applications, the sheath prevents particles in the core from coming into contact with the walls of the channel, thus preventing adhesion and clogging. The sheath also serves to focus the particles or molecules into the center of the channel, allowing for easy counting or measurement through optical or other means.

Sheath flow is a type of laminar flow where a sheath stream surrounds a core stream, with substantial avoidance of mixing between the core stream and the sheath stream. Laminar flow can also be used with fluids of different refractive index to create a waveguide in the core or sheath stream in order to measure transfer of analytes from one stream to the other, or to control the rate of interaction between molecules in one or both streams for carefully controlled chemistry or analysis.

Typically, two-dimensional ("2D") flow focusing approaches use one or more sheath flows to horizontally compress the sample flow towards the center of the flow cell or channel. With such an approach, spatial particle/bead distribution within the flow remains unaffected in the vertical direction. Three-dimensional ("3D") flow focusing controls particle spatial distribution in the vertical dimension by further focusing the sample flow in the vertical direction with three-dimensional sheathed flow with the core stream surrounded on all sides. For "Lab-On-A-Chip" applications, a well defined and dimensionally stable narrow particle/bead flow stream is very desirable. Additionally, three-dimensional sheathed flow (also termed 3D fluidic focusing) mitigates wall flow effects and sample damage, and reduces detection errors due to multiple particle events.

Several approaches have been proposed to achieve 3D flow focusing including: optical gradient focusing [1], groove/chevron focusing [2] and acoustic driven focusing [3], as well as more traditional approaches [4,5] (citations corresponding to these reference numerals appear at the end of this specification). However, for applications such as flow cytometery, these require complex optical beam profiles, precision groove fabrication steps, and/or precision electrical electrode or PZT networks.

A need exists for simplified apparatus for flow focusing while allowing straightforward optical access.

BRIEF SUMMARY

In one embodiment, an apparatus for creating sheathed flow comprises an inlet section comprising an array of tubes including at least one sheath inlet port and a sample inlet port, a flow focusing section downstream from the inlet section, an optical access section downstream from the flow focusing region, and an outlet section downstream from the optical access section, wherein the apparatus is operable to create a three-dimensional sheathed flow around a fluid introduced into the sample inlet port and to maintain such flow through the optical access section.

In a further embodiment, an apparatus for creating sheathed flow comprises an inlet section comprising an array of silica glass capillary tubes including a plurality of sheath inlet ports and a sample inlet port, a flow focusing section downstream from the inlet section, an optical access section downstream from the flow focusing region, and an outlet section downstream from the optical access section, wherein the inlet section, flow focusing section, and optical access section are formed from a single silica glass support tube, and wherein the apparatus is operable to create a three-dimensional sheathed flow around a fluid introduced into the sample inlet port and to maintain the sheathed flow through the optical access section.

In another embodiment, a method of creating a laminar flow comprises providing an apparatus comprising an inlet section comprising an array of tubes including at least one sheath inlet port and a sample inlet port, a flow focusing section downstream from the inlet section, an optical access section downstream from the flow focusing region, and an outlet section downstream from the optical access section, and supplying a sheath fluid through the sheath inlet ports while supplying a sample fluid to the sample inlet port, thereby creating a laminar flow and maintaining such flow through the optical access section.

BRIEF DESCRIPTION OF THE DRAWINGS

FIGS. 3(a), (b), and (c) show still images of the sample focusing by a sheath flow of 400 μL/min with sample flows of 10 μL/min and 100 μL/min, respectively. De-ionized water was used with a color dye added to the sample to enhance its visualization. Top and bottom images are orthogonal views of the 3D flow focusing.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

As used herein, "sheath flow" refers to a subtype of laminar flow where a sheath stream completely surrounds a core stream, and that substantially avoids mixing between the core stream and the sheath stream.

As used herein, the term "sheath fluid" refers to a fluid used in a laminar flow application (including sheath flow) which acts as a carrier with respect to a separate sample fluid. Use of the term "sheath fluid" does not necessarily indicate a sheath flow application.

DESCRIPTION

The described tube array for flow focusing enjoys a number of advantages. It is simple to implement and eliminates the need for complex fabrication steps while preferred embodiments including silica glass capillaries enjoy broad material compatibility. Use of commercial-off-the-shelf (COTS) silica glass tubing, such as capillary tubing, can reduce overall cost, and silica's low optical scatter and fluorescence are advantageous for optical spectroscopy. Furthermore, silica glass construction offers improved flow stability, system rigidity and surface quality compared with polydimethylsiloxane (PDMS) and micro-machined designs. It can use a square cross-section outer tubing, for example of silica glass, which facilitates high optical power probing and manipulation through its optically transparent flat and parallel surfaces. With glass construction, dimensional transitions to smaller cross-sections and a higher fluidic focusing ratio are readily achieved by thermal tapering. Independent control of sheath flow and material parameters allows "reconfigurable" symmetric and asymmetric multi-phase flow focusing and spatial control of the optical properties of sheath flow relative to sample flow. The flow focusing region and the optical access region can be constructed and used independently from each other.

Figure 1:
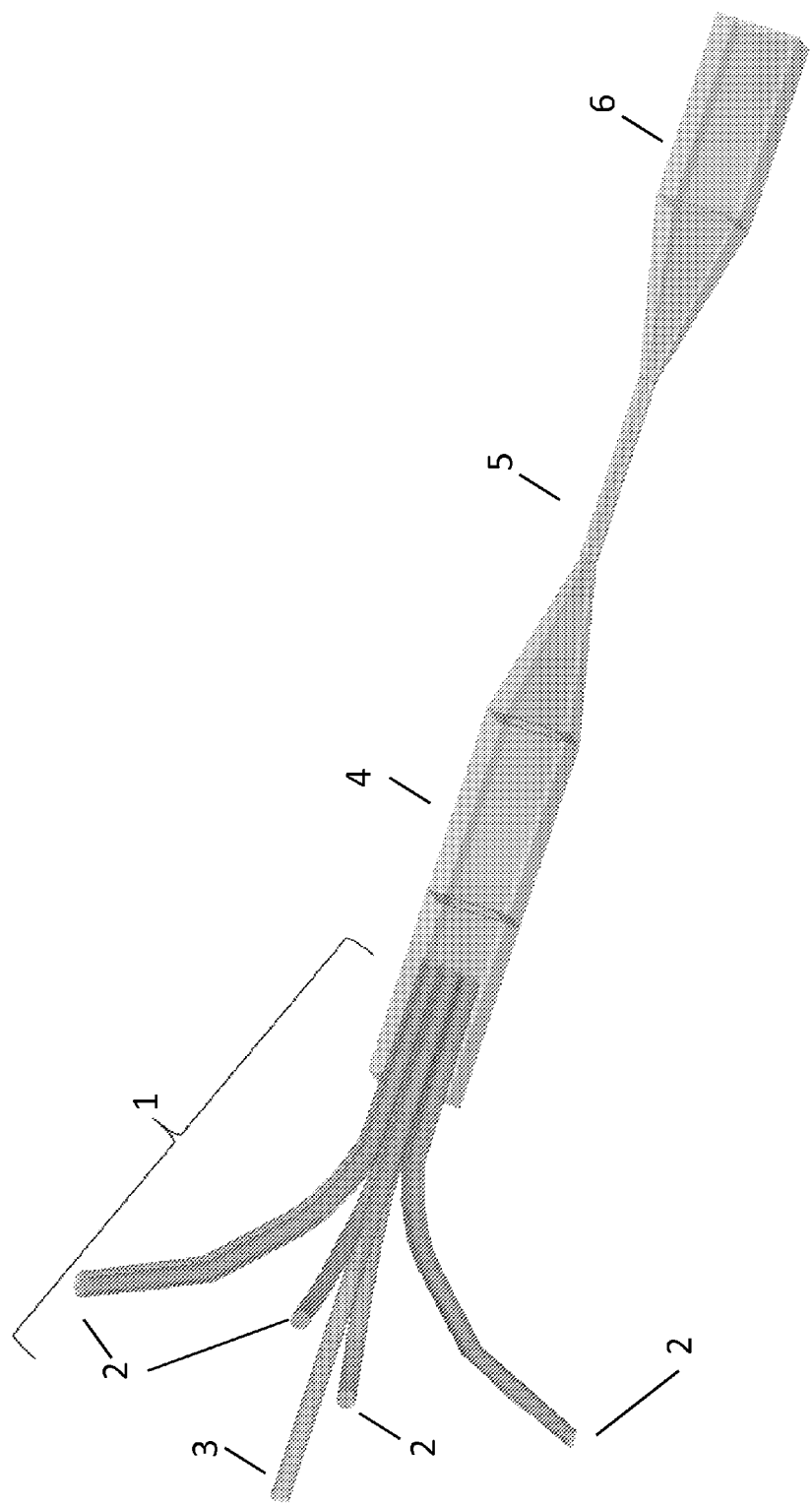
FIG. 1 shows a general scheme of an exemplary apparatus for creating sheathed flow using an array of tubes.

FIG. 1 shows a general scheme of an exemplary apparatus for creating sheathed flow using an array of tubes. An inlet section 1 comprises an array of tubes including a plurality of sheath inlet ports 2 arranged around a single sample inlet port 3. The tubes used for the sheath and sample may be the same or different. A tapered outer support section forms the optical access region that could be used for sample analysis, particle/bead counting and sorting. The taper profile of the outer support section is designed to match the requirements of the desired application and sample particle/bead size. The flow focusing section 4, optical access section 5, and/or outlet section 6 can be constructed and used independently from each other, or optionally may be made as a single unit (e.g., from a support tube as described below), or two units.

While FIG. 1 shows a single outlet port in outlet section 6, other designs are possible such as when sample sorting is required. For example, the apparatus can be constructed with multiple outlet ports that mimic the inlet ports, so that it could be operated in reverse. Multiple outlet ports could also be selected with a fluidic switch so that sheath and/or sample fluid could be independently removed as desired, as in sorting application (such as cell sorting, e.g., fluorescence-activated cell sorting).

The apparatus is capable of creating sheath flow that completely surrounds the sample flow, and to an extent varying with the flow rate ratio between sheath and sample, compresses the sample flow to establish 3D flow focusing via hydrodynamic forces.

The collective sheath flow is preferably supplied via the use of a single pump, so as to establish a stable and uniform pressure-driven flow among the multiplicity of sheath inlet ports. For example, the sheath inlet ports can all be connected to a pump via a single hypodermic syringe, for example in a syringe pump. Other implementations are possible, for example, though the use of multiple pumps that can be independently controlled, it is possible to dynamically control the shape of the sample flow. Also, by independently controlling the sheath material in each sheath inlet port, it is possible to spatially control the optical properties of the sheath. For example, one or more regions of the sheath flow could have an optical absorbing property. In that case, one could establish an attenuating "optical filter" within the optical access region. This particular implementation is expected improve the optical signal to noise ratio for Rayleigh scattering and fluorescence spectroscopy measurements within the optical access region.

Preferably, a second pump is used to establish an independent pressure driven flow of a sample into the sample inlet port. A hypodermic syringe may be used to connect the sample inlet port to the pump.

The flow focusing section, optical access section, and/or outlet section are optionally formed from a support tube, e.g., one having a rectangular or square cross section (optionally of varying diameter, as depicted with 4 and 5 of FIG. 1), and outlet ends of the tubes are enclosed inside an inlet end of the flow focusing section. The support tube may be made of glass (e.g., silica glass) or other suitable material, such as plastic. The sheath fluid and sample fluid exit the array of tubes and travel through an interior space defined by the support tube. In one embodiment, the apparatus consists only of the inlet section comprising an array of tubes, the flow focusing section, the optical access section, and the outlet section, and optionally a polymer binder. In a further embodiment, the flow focusing section, the optical access section, and the outlet section consist only of a single support tube.

The optical access region preferably comprises parallel opposed flat surfaces. Preferably the optical access region (and optionally the entire support tube) has a cross-section that is an equiangular polygon. Such a polygon has an even number of faces n, providing an optical access region having n/2 pairs of opposed parallel sides suitable for flow analysis, particle/bead counting, and/or sorting. For example, a flat square cross-section offers four flat surfaces in two pairs. Analysis techniques can include Rayleigh scattering and/or fluorescence spectroscopy. Other applications of the optical access region are possible.

Figure 2:
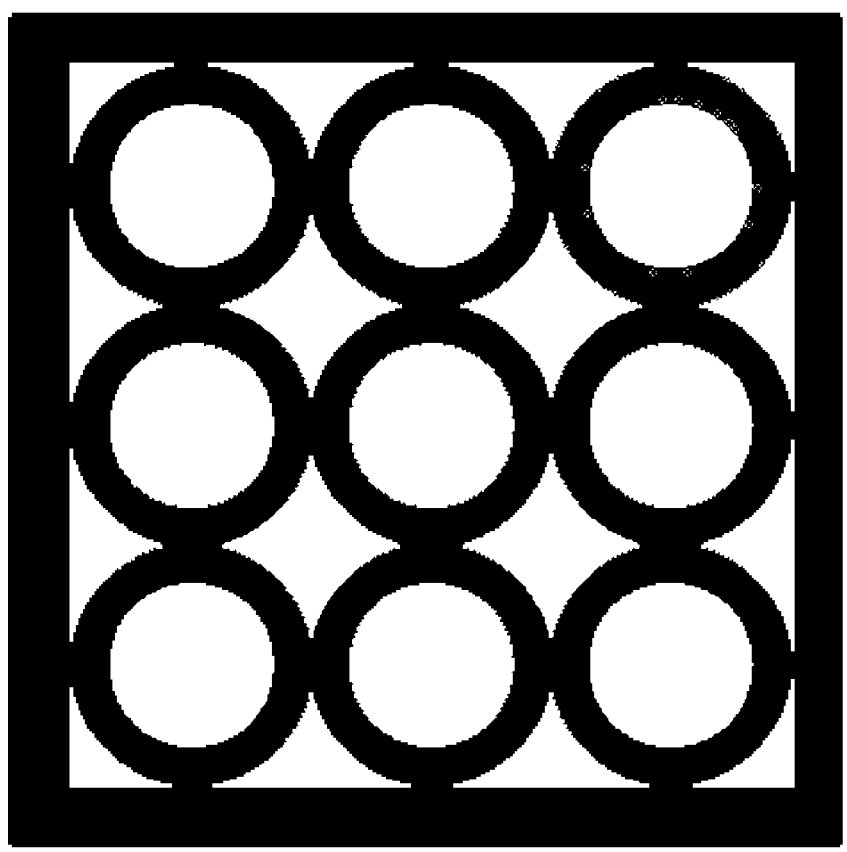
FIG. 2 is a schematic illustration of an exemplary cross-section of an array of tubes for creating sheathed flow.

An exemplary apparatus was constructed including a plurality of sheath inlet ports, a single sample inlet port, and an outer square cross section silica tube support structure—in this apparatus the tubes were silica glass capillary tubes. FIG. 2 depicts a schematic illustration the cross-section of a 3×3 tube array that was formed inside the support tube by inserting nine capillary tubes into a square cross section silica support tube. The total number of inlet tubes in such an array be can varied as desired, and furthermore the array can take a number of forms, such as an m×n rectangular or square grid, or may it have hexagonal close pack or other suitable geometry.

In the example apparatus, the central tube of the 3×3 capillary tube array was used for the sample, with the remaining tubes carrying sheath fluid, thus obtaining sheathed flow. However, the same tube array may carry the sample and sheath fluids in other tubes. For example, the apparatus could be used for 2D focusing by loading sheath fluid in three adjacent tubes in top and bottom rows of the array, with the same sample fluid loaded in the three adjacent tubes in the middle row of the array. Moreover, laminar, non-sheathed flow could be had with four sample fluids (optionally four different sample fluids) loaded through the corner tubes of FIG. 2, separated by sheath fluid in the remaining tubes. Numerous other loading schemes are possible, particular with larger arrays. In this way, the disclosed apparatus suitable for 3D fluidic focusing might be used to conduct 2D focusing.

The downstream or outlet ends of the array of tubes may be flush with one another, or alternately some tubes may extend further downstream than others. In a preferred embodiment, the sample inlet port(s) extend further downstream than the sheath inlet port, as this was found to improve 3D focusing in some circumstances.

In the exemplary apparatus, interstitial spaces between the capillary tube elements and the inlet section of the support tube were sealed with a thermoplastic epoxy. Other suitable polymeric adhesives could be substituted for the epoxy to bind the tubes to one another and/or to the flow focusing section. An alternate implementation would locally thermally fuse the individual tubes to form a single tube array, and then locally fuse the array to the flow focusing section to form an "all silica" microstructure without requiring secondary bonding agents. Combinations of such binding techniques are possible (e.g., glass tubes are fused to each other in an array and then bound to the inlet section with an adhesive). The binding is preferably operable to create a seal between the array of tubes and the inlet section.

In the exemplary implementation, the sheath and sample inlet ports were nine polyamide-coated silica capillary tubes having about 160 µm outer diameter and about 99 µm inner diameter. Suitable capillary tubing is readily available with interior diameters ranging from 0.05 mm to 2.00 mm in silica glass and other materials. One should select tubing with a diameter suitable to prevent clogging. The support tube consisted of a silica square cross section tubing with about 1000 µm×1000 µm outer dimensions and about 500 µm×500 µm inner dimensions, tapered as described below. Other tubing dimensions, shapes and materials are possible depending on the application requirements, and one of ordinary skill in the art can modify commercial tubing using a puller to obtain other dimensions as desired. Commercial suppliers such as VitroCom and Polymicro Technologies offer a wide variety of suitable tubing products having round, rectangular, and square cross sections.

Although preferred embodiments employ capillary tubing, it is expected that tubing of larger sizes could operate to create the desired flow patterns if suitable flow rate and other fluidic parameters were used. Moreover, although preferred embodiments operate with liquids, operation with gasses should be possible as well.

In the exemplary device, the flow focusing, optical access, and outlet sections took the form of a single support tube. Silica glass tubing with a square cross section was thermally tapered and included a down-taper region about 10 mm long, a constant cross section region about 10 mm long and an up-taper region about 5 mm long. The outside and inside dimensions of the constant square cross section microstructure region where about 120 µm and 60 µm, respectively. Other taper profiles and dimensions are possible depending on the application and particle/bead size.

Figure 3:
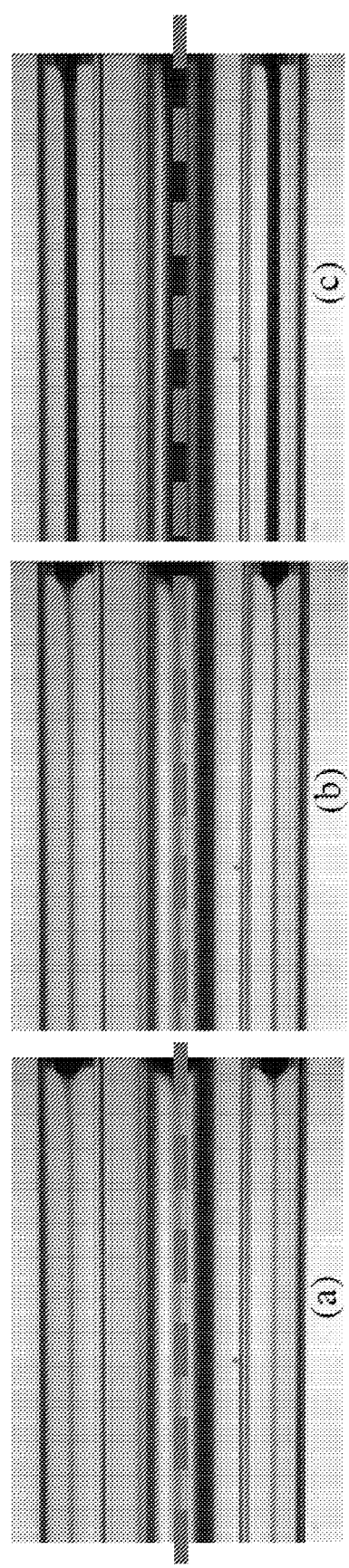
FIG. 3 illustrates flow through an optical access section at various flow rate ratios for the sheath and sample flow (the latter is also termed core flow).

FIG. 3 illustrates flow through an optical access section at various flow rate ratios for the sheath and sample flow. FIGS. 3(a), (b), and (c) show still images of the sample focusing by a sheath flow of 400 µL/min with sample flows of 1 µL/min, 10 µL/min and 100 µL/min, respectively. Top and bottom images are orthogonal views of the 3D flow focusing—the central region in each image in the vicinity of the dashed line is an out-of-focus third view that appears as an artifact of the method used to acquire the images, and can be disregarded. De-ionized water was used with a color dye added to the sample to enhance its visualization as compared to the uncolored sheath flow. In an actual application, the sample flow may be any suitable fluid, which may also contain additives such as biological cells, fluorescent particles, or colored beads.

As seen in FIG. 3, the flow focusing effect was strong throughout a wide range of flow rate ratios. This flow stability is an improvement over previously-described designs. Furthermore, varying the ratios allowed for control of the shape of the sample flow.

Figure 4:
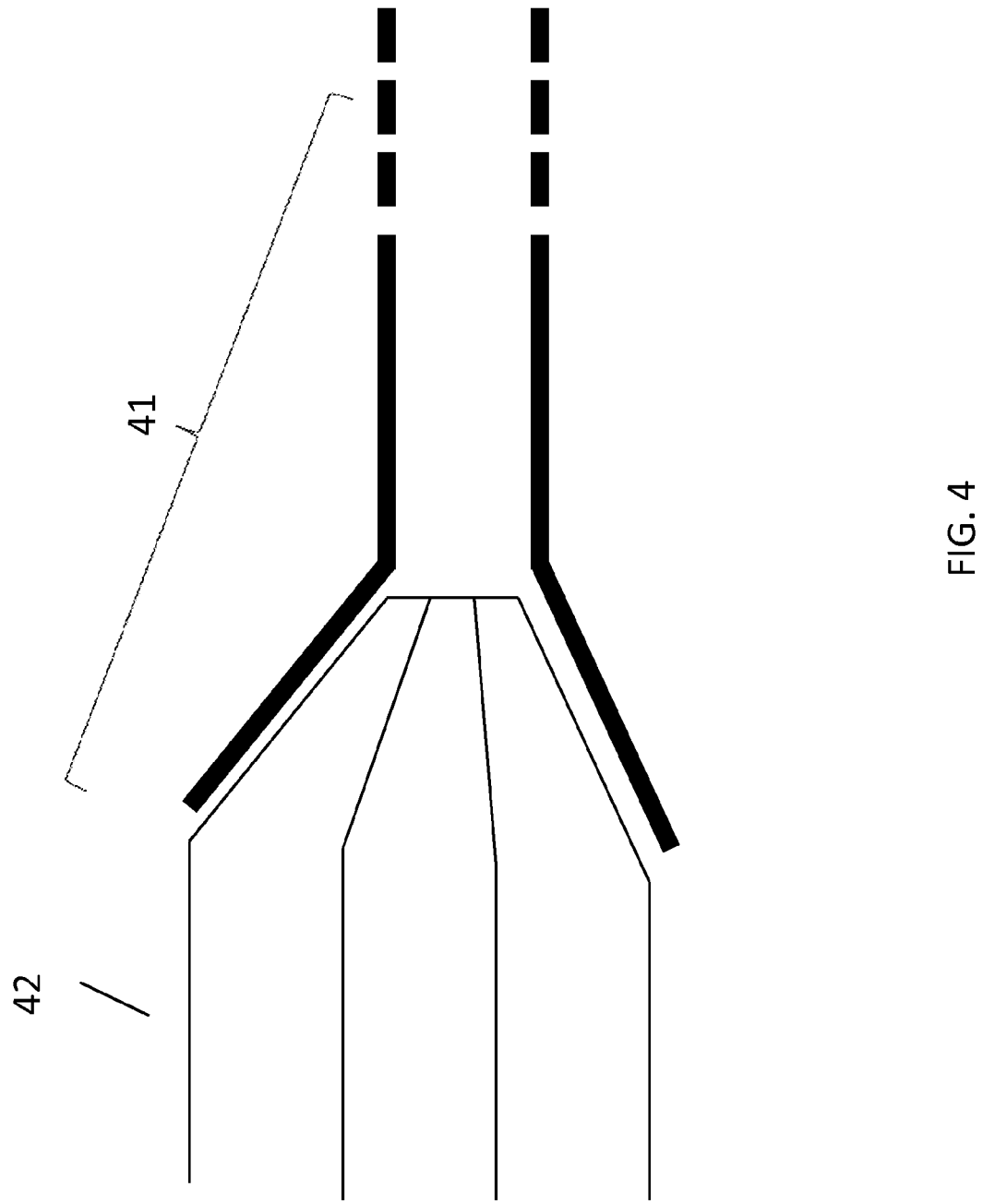
FIG. 4 shows a side section view of an embodiment having a tapered array of tubes in an inlet section.

FIG. 4 shows a side section schematic view of an embodiment having a tapered array of tubes 42 in a tapered flow focusing section 41. By fusing glass tubes into an array and then heating and pulling the array of glass tubes, a tapered shape can be achieved while maintaining the cross-sectional shape Likewise, the flow focusing section 41, or optionally a support tube comprising the flow focusing section 41 in addition to the downstream sections not depicted in FIG. 4, can be similarly tapered.

The described apparatus is easily made in a compact form factor, making it well suited to portable analytic devices, unlike certain prior art approaches. It also is able to perform either 3D or 2D focusing.

The described tube array for focusing shares further advantages over previously described techniques. As compared to commercial 3D microfluidic nozzles, it is more suitable to fast flows and more compact. Optical gradient focusing suffers from weak focusing forces, lack of suitability for fast flows, and the need for complex optics required for generation of optical beam shape. Groove/chevron focusing requires precise flow control and complex fabrication techniques, particularly if high surface quality of the inner walls is desired (a featuring arising more naturally with glass capillaries). Acoustic-driven focusing is not suitable for fast flows, has limited spatial focusing, and requires a resonant acoustic structure.

All documents mentioned throughoutt this application are hereby incorporated by reference in their entirety.

REFERENCES

1. Y. Zhao, B. S. Fujimoto, G. D. M. Jeffries, P. G. Schiro and D. T. Chui, "Optical gradient flow focusing", Optics Express, Vol. 15, No. 10, pp. 6167-6175 (2007)
2. P. B. Howell, J. P. Golden, L. R. Hilliard, J. S. Erickson, D. R. Mott and F. S. Ligler, "Two simple and rugged designs for creating microfluidic sheath flow", Lab Chip, Vol, 8, pp. 1097-1103 (2008).
3. G. Goddard, J. C. Martin, S. W. Graves and G. Kaduchak, "Ultrasonic particleconcentration for sheathless focusing of particles for analysis in a flow MICROSTRUCTURE", Cytometry Part A, Vol. 69A, pp. 66-74 (2006)
4. V. Kachel, H. Fellner-Feldegg, and E. Menke, "Hydrodynamic Properties of Flow Cytometry Instruments," Flow cytometry and sorting, 2nd Edition, Wiley-Liss Inc. pp. 27-44 (1990)

5. R. Miyake, H. Ohki, I. Yamazaki and R. Yabe, "Development of Micro Sheath Flow Chambers," Proc. Of IEEE Micro Mechanical Systems Workshop, Nara, Japan, pp. 259-264 (1991).

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. An apparatus for creating sheathed flow, comprising:
    an inlet section comprising an m×n array of tubes where m and n are each independently 3 or greater, including a plurality of sheath inlet ports and a sample inlet port,
    a flow focusing section downstream from the inlet section,
    an optical access section downstream from the flow focusing region, and
    an outlet section downstream from the optical access section,
    wherein the apparatus is operable to create a three-dimensional sheathed flow around a fluid introduced into the sample inlet port and to maintain such flow through the optical access section,
    wherein outlet ends of the array of tubes are flush with one another.

2. The apparatus of claim 1, configured for independent control of sheath flow in each sheath inlet port.

3. The apparatus of claim 1, wherein said tubes are capillary tubes made of silica glass.

4. The apparatus of claim 1, wherein:
    (a) individual tubes in said array of tubes are silica glass and are fused to one another, or
    (b) individual tubes in said array of tubes are bound to one another with a polymer.

5. The apparatus of claim 1, wherein:
    (a) said array of tubes and said inlet section both comprise silica glass and are fused to one another, or
    (b) said array of tubes is bound to said inlet section with a polymer.

6. The apparatus of claim 1, wherein a single support tube forms said flow focusing section, optical access section, and outlet section.

7. The apparatus of claim 6, wherein said capillaries and/or said support tube are tapered.

8. The apparatus of claim 1, wherein said optical access region comprises parallel opposed flat surfaces.

9. The apparatus of claim 1, wherein said outlet section comprises a plurality of outlet ports.

10. The apparatus of claim 9, further comprising a fluidic switch operably connected between said optical access section and said plurality of outlet ports.

11. An apparatus for creating sheathed flow, comprising:
    an inlet section comprising an m×n array of tubes where m and n are each independently 3 or greater, including a plurality of sheath inlet ports and a sample inlet port,
    a flow focusing section downstream from the inlet section,
    an optical access section downstream from the flow focusing region, and
    an outlet section downstream from the optical access section,
    wherein the apparatus is operable to create a three-dimensional sheathed flow around a fluid introduced into the sample inlet port and to maintain such flow through the optical access section, and
    wherein an outlet end of the sample inlet port extends further downstream than outlet ends of said at least one sheath inlet port.

12. A flow cytometer comprising the apparatus of claim 1.

13. An optical waveguide comprising the apparatus of claim 1.

14. A method of creating a laminar flow, comprising:
    providing an apparatus comprising
        an inlet section comprising an m×n array of tubes where m and n are each independently 3 or greater, including a plurality of sheath inlet ports and a sample inlet port,
        a flow focusing section downstream from the inlet section, an optical access section downstream from the flow focusing region, and
        an outlet section downstream from the optical access section; and
    supplying a sheath fluid through the sheath inlet ports while supplying a sample fluid to the sample inlet port, thereby creating a laminar flow around the sample fluid and maintaining such flow through the optical access section,
    wherein outlet ends of the array of tubes are flush with one another.

15. The method of claim 14, wherein said laminar flow is three-dimensional sheathed flow that is maintained through the optical access section.

16. The method of claim 14, wherein said outlet section comprises at least two outlet ports, and further comprising switching said laminar flow between the at least two outlet ports.

17. The method of claim 14, wherein said sheath fluid and/or sample fluid comprises at least two different fluids differing in optical properties.

18. The method of claim 14, wherein flow through each sheath inlet port is independently controlled.

* * * * *